(12) United States Patent
Militzer et al.

(10) Patent No.: US 10,894,805 B2
(45) Date of Patent: Jan. 19, 2021

(54) PRODRUGS OF THE SELECTIVE PROGESTERONE RECEPTOR MODULATOR (SPRM) (11.BETA.,17.BETA.)-17-HYDROXY-11-[4-(METHYLSULPHONYL)PHENYL]-17-(PENTAFLUOROETHYL)ESTRA-4,9-DIEN-3-ONE

(71) Applicant: BAYER PHARMA AKTIENGESELLSCHAFT, Berlin (DE)

(72) Inventors: Hans-Christian Militzer, Odenthal (DE); Antje Rottmann, Berlin (DE); Andrea Wagenfeld, Berlin (DE); Horst Irlbacher, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 70 days.

(21) Appl. No.: 16/082,025

(22) PCT Filed: Mar. 1, 2017

(86) PCT No.: PCT/EP2017/054704
§ 371 (c)(1),
(2) Date: Sep. 4, 2018

(87) PCT Pub. No.: WO2017/148977
PCT Pub. Date: Sep. 8, 2017

(65) Prior Publication Data
US 2019/0367555 A1      Dec. 5, 2019

(30) Foreign Application Priority Data
Mar. 4, 2016 (EP) ..................... 16158598

(51) Int. Cl.
C07J 31/00 (2006.01)
A61P 5/36 (2006.01)

(52) U.S. Cl.
CPC ............. *C07J 31/006* (2013.01); *A61P 5/36* (2018.01)

(58) Field of Classification Search
CPC .................................................. C07J 31/006
See application file for complete search history.

(56) References Cited

U.S. PATENT DOCUMENTS

| | | | |
|---|---|---|---|
| 6,316,432 B1 | 11/2001 | Schwede et al. | |
| 6,503,895 B2 | 1/2003 | Schwede et al. | |
| 6,806,263 B2 | 10/2004 | Schwede et al. | |
| 7,148,213 B2 | 12/2006 | Schwede et al. | |
| 8,053,426 B2 * | 11/2011 | Fuhrmann | C07J 51/00 514/179 |
| 8,278,469 B2 * | 10/2012 | Schwede | A61P 35/00 552/648 |
| 9,085,603 B2 * | 7/2015 | Schwede | A61P 15/18 |
| 9,109,004 B2 * | 8/2015 | Schwede | A61P 15/18 |
| 9,717,739 B2 | 8/2017 | Schwede et al. | |
| 10,155,004 B2 | 12/2018 | Schwede et al. | |
| 2012/0149670 A1 | 6/2012 | Schwede et al. | |
| 2016/0296534 A1 | 10/2016 | Shuett et al. | |
| 2019/0367555 A1 | 12/2019 | Militzer et al. | |

FOREIGN PATENT DOCUMENTS

| | | |
|---|---|---|
| CL | 2004001191 A1 | 3/2005 |
| CL | 2007003266 A1 | 7/2008 |
| CL | 2012000166 A1 | 8/2012 |
| CL | 2015003014 A1 | 4/2016 |
| CL | 201802516 A1 | 2/2019 |
| EA | 201200121 A1 | 7/2012 |
| EP | 2983671 A1 | 2/2016 |
| JP | 2002233378 A | 8/2002 |
| WO | 9834947 A1 | 8/1998 |
| WO | 99/45127 A2 | 9/1999 |
| WO | 02067910 A2 | 9/2002 |
| WO | 2008058767 A1 | 5/2008 |
| WO | 2011/009531 | 1/2011 |
| WO | 2014/166971 A1 | 10/2014 |
| WO | 2017/148977 A1 | 9/2017 |
| WO | 2017152076 A1 | 9/2017 |

OTHER PUBLICATIONS

International Search Report for PCT/EP2017/054704, dated Apr. 24, 2017, 3 pages.

Endo et al., "Characterization of rat and mouse Nad<+>-dependent 3alpha/17beta/20alpha-hydroxysteroid dehydrogenases and identification of substrate specificity determinants by site-directed mutagenesis", Archives of Biochemistry and Biophysics, vol. 467, No. 1, Oct. 25, 2007, pp. 76-86.

(Continued)

*Primary Examiner* — Golam M Shameem
(74) *Attorney, Agent, or Firm* — McBee Moore & Vanik IP, LLC

(57) ABSTRACT

This invention concerns Selective Progesterone Receptor Modulators (SPRM) in a prodrug form as well as their application in therapy. (3α, 11β,17β)-1 1-[4-(methylsulfonyl)phenyl]-17-(pentafluoroethyl)estra-4,9-diene-3,17-diol (Compound 1) is one of the invention prodrugs.

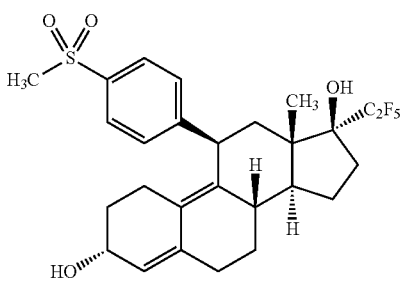

12 Claims, 1 Drawing Sheet

(56) References Cited

OTHER PUBLICATIONS

Blom et al., "Metabolism of Norethisterone and Norethisterone Derivatives in Rat Uterus, Vagina, and Aorta", Drug Metabolism and Disposition, vol. 29, No. 7, Jul. 1, 2001, pp. 976-982.
Smirnova, O.V., "Competitive Agonists and Antagonists of Nuclear Steroid Receptors: Evolution or Alignment of a Concept," Biochemistry ( БИОХИМИЯ ), (2015), vol. 80, Issue 10: 1493-1502.

* cited by examiner

PRODRUGS OF THE SELECTIVE PROGESTERONE RECEPTOR MODULATOR (SPRM) (11.BETA.,17.BETA.)-17-HYDROXY-11-[4-(METHYLSULPHONYL)PHENYL]-17-(PENTAFLUOROETHYL)ESTRA-4,9-DIEN-3-ONE

This application is the U.S. national phase of International Application No. PCT/EP2017/054704 filed 1 Mar. 2017, which designated the U.S. and claims priority to EP Patent Application No. 16158598.9 filed 4 Mar. 2016, the entire contents of each of which are hereby incorporated by reference.

The invention concerns Selective Progesterone Receptor Modulators (SPRM) in a prodrug form as well as to their application in therapy. The concerned Selective Progesterone Receptor Modulators (SPRM) are described in WO2011/009531A1. Prodrugs were surprisingly found. The invention is further directed to methods of preparing said compounds, pharmaceutical compositions, and the use of said compounds for manufacturing pharmaceutical compositions for the treatment or prophylaxis of diseases such as gynaecological diseases and for fertility control and emergency contraception. Preferably, the gynaecological diseases are Uterine Fibroids or Endometriosis as well as known associated symptoms thereof like pelvic pain, infertility, Heavy Menstrual Bleeding and bleeding between menstruation periods. The prodrugs are useful as a sole agent or in combination with other active ingredients.

BACKGROUND

Selective Progesterone Receptor Modulators (SPRM) such as RU 486/Mifepristone in EP0057115A3 became first known in 1982 and have been described many times since then. The effect of RU 486/Mifepristone on the immunohistochemical distribution of prostaglandin E and its metabolite in decidual and chorionic tissue in early pregnancy was investigated by Cheng, L, et al in J Clin Endocrinol Metab, 1993; 77:873-877.

Asoprisnil (J867) was identified as a Selective Progesterone Receptor Modulator (SPRM) useful for gynecological therapy; see Deborah DeManno et al. (Steroids 68 (2003) 1019-1032). The data presented herein demonstrated that both Asoprisnil and its major metabolite J912 exhibit partial agonist/antagonist effects in various animal models. Progesterone binding affinity of Asoprisnil (J867) was about 299% Relative molar Binding Affinity (RBA) whereas J912 showed a Progesterone binding affinity of about 165% RBA.

Other fluorinated 17α-side chain progesterone receptor antagonist steroids were published in WO98/034947 and Fuhrmann et al., J. Med. Chem. 43, 5010-5016 (2000).

Biotransformation of 5(10)-estrene-3α,17β-diol in stallion testes is discussed in Dumasia et al. (631$^{st}$ Meeting, Guildford, vol 17, 1989, p 1019-1020).

SUMMARY

Selective Progesterone Receptor Modulators (SPRM) are described in WO2011/009531A1 for the prophylaxis or treatment of disease(s) such as gynaecological diseases and for fertility control and emergency contraception. The present invention is now directed to prodrugs of Selective Progesterone Receptor Modulators (SPRM) as disclosed in WO2011/009531A1 and encompassed herein. It was surprisingly found that Compound 1 as disclosed below is a potent prodrug of one of the SPRMs as described in WO2011/009531A1. This prodrug is useful for the prophylaxis or treatment of disease(s) such as gynaecological diseases. The present invention is directed to an alternative method for the prophylaxis or treatment of gynaecological diseases wherein the active ingredient is obtained after metabolization of the prodrug in the body.

DESCRIPTION

Figure 1:
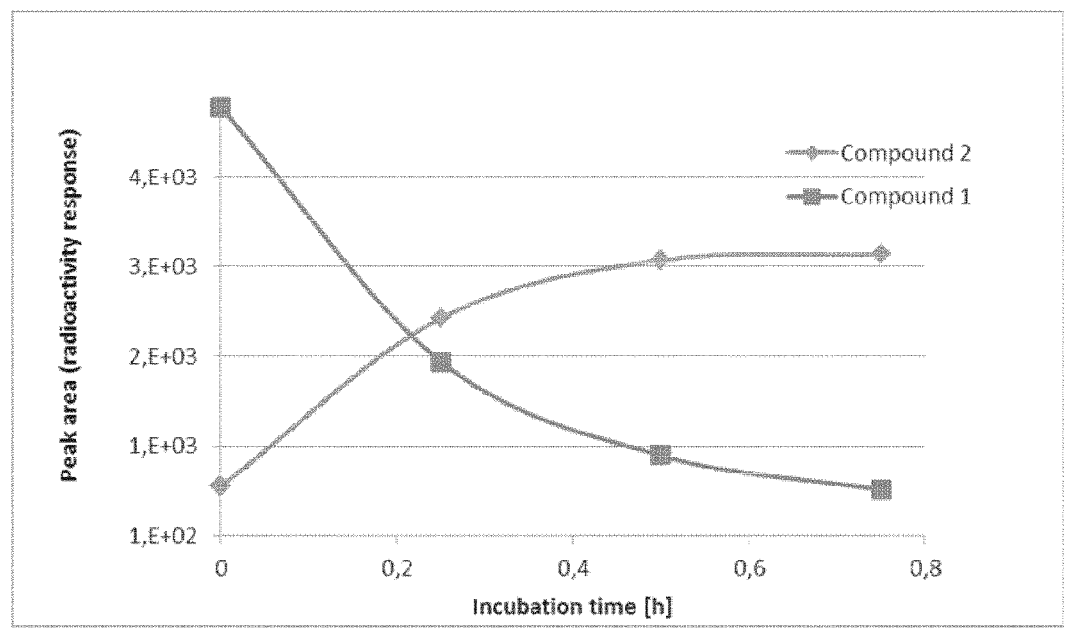
FIG. 1 depicts concentration-time course of Compound 2 and Compound 1 after incubation of Compound 1 in human liver microsomes.

In a first aspect, the invention is directed to a prodrug of a Selective Progesterone Receptor Modulator (SPRM).

In a further embodiment, the invention is directed to prodrugs where the Selective Progesterone Receptor Modulator (SPRM) is one of the compounds as disclosed in WO2011/009531A1 and encompassed herein. More preferably, the Selective Progesterone Receptor Modulator (SPRM) is (11β,17β)-17-Hydroxy-11-[4-(methylsulphonyl)phenyl]-17-(pentafluoroethyl)estra-4,9-dien-3-one as described below (Compound 2)

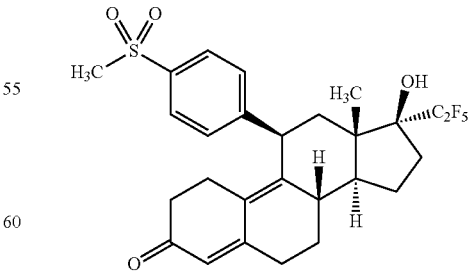

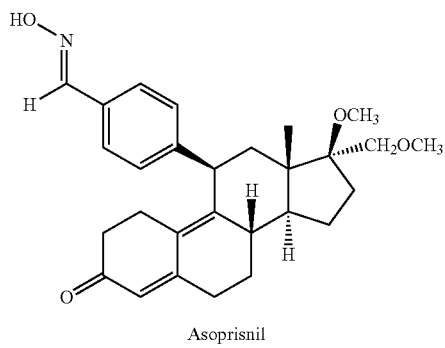

Asoprisnil or a pharmaceutically acceptable salt thereof.

In a further embodiment, the invention is directed to a Prodrug where the Prodrug is a Progesterone derivative and with the proviso that the Progesterone derivative is never a compound that is substituted with an Alkylsulphonimidoyl moiety at the 11-phenyl or 11-biphenyl of the Progesterone derivative.

Preferably, the Alkylsulphonimidoyl moiety is at the position 4 of the 11-phenyl ring or 11-biphenyl. Alkyl is a $C_1$-$C_6$ alkyl. Preferably, alkyl is methyl.

Preferably, the Progesterone derivative is substituted at the position 17 with Hydroxyl and pentafluoroethyl.

More preferably, the Prodrug is never the following compounds (11β,17β)-17-hydroxy-11-[4-(RS-methylsulphonimidoyl)phenyl]-17-(pentafluoroethyl)estra-4,9-dien-3-one with the formula as described below (Compound 3)

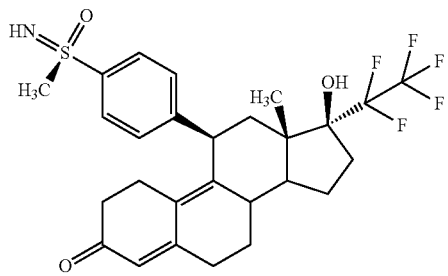

and/or (11β,17β)-17-hydroxy-11-[4'-(RS-methylsulphonimidoyl)biphenyl-4-yl]-17-(pentafluoroethyl)estra-4,9-dien-3-one (Compound 4)

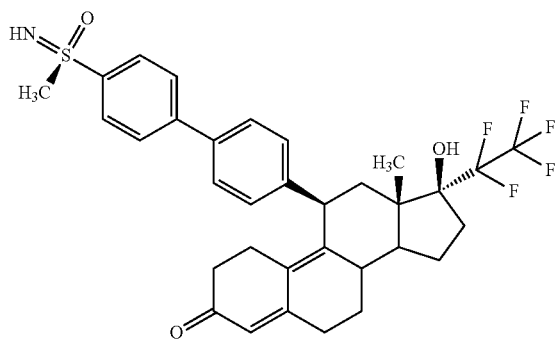

or a pharmaceutically acceptable salt thereof.

Even more preferably, the Prodrug is never Compound 3.

In a preferred embodiment, the invention is directed to a prodrug of a Selective Progesterone Receptor Modulator (SPRM) where the SPRM is selected from (11β,17β)-17-Hydroxy-11-[4-(methylsulphonyl)phenyl]-17-(pentafluoroethyl)estra-4,9-dien-3-one as described below (Compound 2)

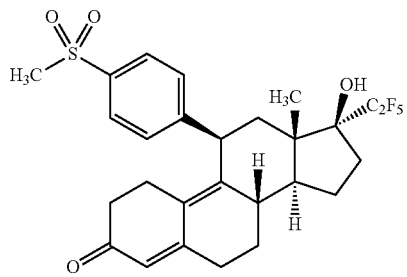

or a pharmaceutically acceptable salt thereof and/or
the prodrug is selected from (3α,11β,17β)-11-[4-(methylsulfonyl)phenyl]-17-(pentafluoroethyl)estra-4,9-diene-3,17-dial as described below (Compound 1)

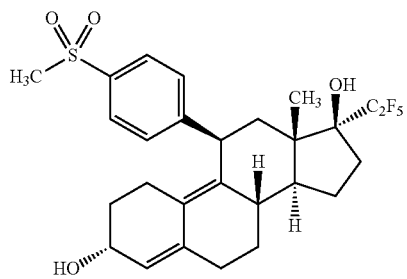

or a pharmaceutically acceptable salt thereof.

Therefore, (3α,11β,17β)-11-[4-(methylsulfonyl)phenyl]-17-(pentafluoroethyl)estra-4,9-diene-3,17-diol (Compound 1) is a prodrug of (11β,17β)-17-Hydroxy-11-[4-(methylsulphonyl)phenyl]-17-(pentafluoroethyl)estra-4,9-dien-3-one (Compound 2) that is a SPRM as described in WO2011/009531A1.

In a second aspect, the invention is directed to a method for obtaining a prodrug of a Selective Progesterone Receptor Modulator (SPRM).

Preferably, the Selective Progesterone Receptor Modulator (SPRM) is one of the compounds as disclosed in WO2011/009531A1 and encompassed herein. More preferably, the Selective Progesterone Receptor Modulator (SPRM) is (11β,17β)-17-Hydroxy-11-[4-(methylsulphonyl)phenyl]-17-(pentafluoroethyl)estra-4,9-dien-3-one as described below (Compound 2)

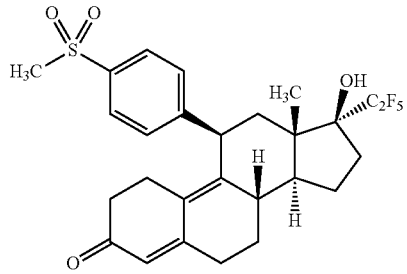

or a pharmaceutically acceptable salt thereof.

In a preferred embodiment, the invention is directed to a method for obtaining the invention prodrug of a Selective Progesterone Receptor Modulator (SPRM) where the SPRM is selected from (11β,17β)-17-Hydroxy-11-[4-(methylsulphonyl)phenyl]-17-(pentafluoroethyl)estra-4,9-dien-3-one as described below (Compound 2)

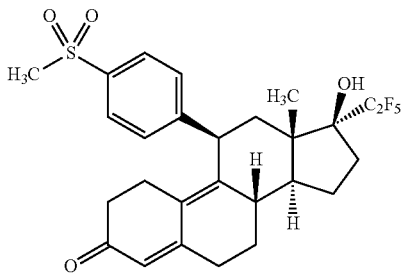

or a pharmaceutically acceptable salt thereof and/or
the prodrug is selected from (3α,11β,17β)-11-[4-(methylsulfonyl)phenyl]-17-(pentafluoroethyl)estra-4,9-diene-3,17-diol as described below (Compound 1)

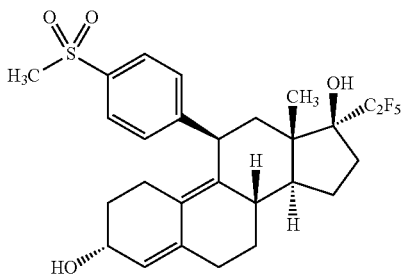

or a pharmaceutically acceptable salt thereof.

In other words, the invention is directed to a method for obtaining (3α,11β,17β)-11-[4-(methylsulfonyl)phenyl]-17-(pentafluoroethyl)estra-4,9-diene-3,17-diol (Compound 1) comprising the reduction step where (11β,17β)-17-hydroxy-11-[4-(methylsulfonyl)phenyl]-17-(pentafluoroethyl)estra-4,9-dien-3-one (Compound 2) is reacted in presence of a reducing agent.

Reduction step is completed in presence of a reducing agent. Reducing agents are well known in the art. Preferably, the reducing agent is selected from sodium borohydride, Lithiumaluminiumhydride (LiAlH4), Lithiumborohydride (LiBH4), Diisobutylaluminiumhydride ((i-Bu)2AlH). More preferably, the reducing agent is sodium borohydride.

In a further embodiment, the invention is directed to a method for obtaining the invention prodrug of a Selective Progesterone Receptor Modulator (SPRM) comprising a biochemical reaction catalysed by Aldo-Keto Reductase (AKR) enzymes. The reaction is conducted in-vitro or in-vivo, preferably in-vitro.

The methods are applicable to all invention prodrugs as described above.

In a third aspect, the invention is directed to a prodrug of a Selective Progesterone Receptor Modulator (SPRM) useful as a therapeutical drug for treating and/or prophylaxis of gynaecological diseases or for fertility control and emergency contraception.

Preferably, the Selective Progesterone Receptor Modulator (SPRM) is one of the compounds as disclosed in WO2011/009531A1 and encompassed herein. More preferably, the Selective Progesterone Receptor Modulator (SPRM) is (11β,17β)-17-Hydroxy-11-[4-(methylsulphonyl)phenyl]-17-(pentafluoroethyl)estra-4,9-dien-3-one as described below (Compound 2)

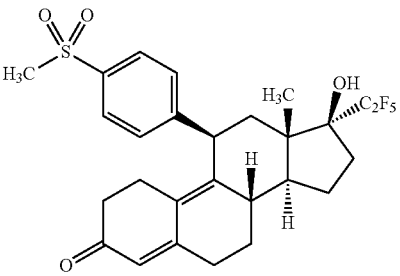

or a pharmaceutically acceptable salt thereof.

In a preferred embodiment, the invention is directed to a prodrug of a Selective Progesterone Receptor Modulator (SPRM)
where
the SPRM is selected from (11β,17β)-17-Hydroxy-11-[4-(methylsulphonyl)phenyl]-17-(pentafluoroethyl)estra-4,9-dien-3-one as described below (Compound 2)

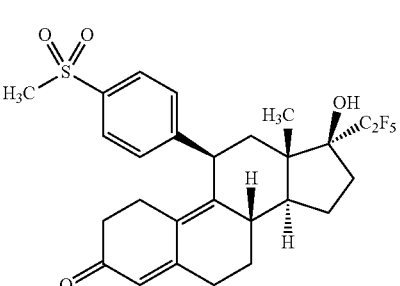

or a pharmaceutically acceptable salt thereof and/or
the prodrug is selected from (3α,11β,17β)-11-[4-(methylsulfonyl)phenyl]-17-(pentafluoroethyl)estra-4,9-diene-3,17-diol as described below (Compound 1)

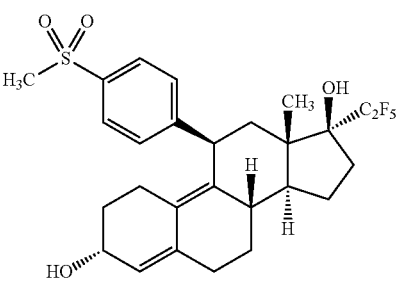

or a pharmaceutically acceptable salt thereof
that is useful as a therapeutical drug for treating and/or prophylaxis of gynaecological diseases or for fertility control and emergency contraception.

Therefore, the invention is directed to a prodrug (3α,11β,17β)-11-[4-(methylsulfonyl)phenyl]-17-(pentafluoroethyl)estra-4,9-diene-3,17-diol (Compound 1) that is useful as therapeutical drug for treating and/or prophylaxis of gynaecological diseases or for fertility control and emergency contraception.

Preferably, the gynaecological disease is selected from Uterine Fibroids, Endometriosis and hormone-dependent breast cancers. More preferably, the gynaecological disease is selected from Uterine Fibroids or Endometriosis. Even more preferably, the gynaecological disease is Uterine Fibroids. Even more preferably, the gynaecological disease is Endometriosis.

In other word, the invention is directed to the use of (3α,11β,17β)-11-[4-(methylsulfonyl)phenyl]-17-(pentafluoroethyl)estra-4,9-diene-3,17-diol (Compound 1) as a prodrug.

More preferably, the gynaecological diseases are selected from Uterine Fibroids and Endometriosis and symptoms thereof.

Most common symptoms related to Uterine Fibroids are pelvic pain, infertility, Heavy Menstrual Bleeding (HMB) and bleeding or spotting between menstruation periods. Preferably, treated symptom is Heavy Menstrual Bleeding (HMB).

Most common symptoms related to Endometriosis are pelvic pain and Dysmenorrhoea (i.e. excessive pain during menstruation), Dyspareunia (i.e. painful sexual intercourse) and infertility. Preferably, treated symptom is Dysmenorrhoea.

The invention prodrug is administered to patient during a period of twelve (12) weeks up to twenty-four (24) weeks followed by a break period wherein administration of Compound 1 is discontinued until one (1) or two (2) menstrual bleeding episodes occur; optionally administration and break periods are repeated at least one (1) time. Treatment is repeated as much as necessary like two (2) to four (4) times. If no menstrual bleeding episode occurs after disruption of treatment then treatment is re-started on demand, due to return of symptoms or disease positively diagnosed, after a break period corresponding to the standard time between two (2) menstrual bleeding episodes (21-45 days).

A menstrual bleeding episode is at least one day of menstrual bleeding.

The invention prodrug is administered daily to patient at the dosage of about 0.5 to 10 mg per unit dosage, preferably 0.5 to 5 mg per unit dosage.

The invention prodrugs are as described above.

In a fourth aspect, the invention is directed to a pharmaceutical composition comprising a prodrug of a Selective Progesterone Receptor Modulator (SPRM) and a pharmaceutically acceptable excipient or carrier.

Preferably, the Selective Progesterone Receptor Modulator (SPRM) is one of the compounds as disclosed in WO2011/009531A1 and encompassed herein. More preferably, the Selective Progesterone Receptor Modulator (SPRM) is (11β,17β)-17-Hydroxy-11-[4-(methylsulphonyl)phenyl]-17-(pentafluoroethyl)estra-4,9-dien-3-one as described below

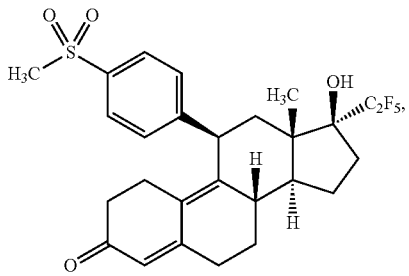
(Compound 2)

or a pharmaceutically acceptable salt thereof.

Preferably, the pharmaceutical composition comprises a prodrug that is selected from (3α,11β,17β)-11-[4-(methylsulfonyl)phenyl]-17-(pentafluoroethyl)estra-4,9-diene-3,17-diol as described below

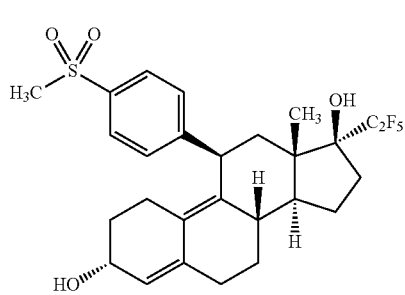
(Compound 1)

or a pharmaceutically acceptable salt thereof.

The pharmaceutical composition comprises the invention prodrug at the dosage of about 0.5 to 10 mg per unit dosage, preferably 0.5 to 5 mg per unit dosage.

In a further embodiment, the pharmaceutical composition comprises the invention prodrug optionally admixed with a pharmaceutically acceptable excipient or carrier.

The invention prodrugs are as described above.

The pharmaceutically acceptable excipient includes carriers, solvents, or stabilizers.

The person skilled in the art is familiar with excipients which are suitable for the desired pharmaceutical formulations, preparations or compositions on account of his/her expert knowledge.

The administration of the compounds, pharmaceutical compositions according to the invention is performed in any of the generally accepted modes of administration available in the art (intravenous, oral, parenteral, pulmonary, nasal, sublingual, lingual, buccal, rectal, vaginal route or as an implant or stent, etc. . . . ). Oral deliveries are preferred.

The pharmaceutical compositions can be utilised to achieve the desired pharmacological effect by administration to a patient in need thereof. A patient, for the purpose of this invention, is a mammal, preferably a human. Preferably, the patient is a woman.

In a fifth aspect, the invention is directed to the use of a prodrug of a Selective Progesterone Receptor Modulator (SPRM) for the manufacture of a therapeutical drug for treating and/or prophylaxis of gynaecological diseases or for fertility control and emergency contraception.

Preferably, the Selective Progesterone Receptor Modulator (SPRM) is one of the compounds as disclosed in WO2011/009531A1 and encompassed herein. More preferably, the Selective Progesterone Receptor Modulator (SPRM) is (11β,17β)-17-Hydroxy-11-[4-(methylsulphonyl)phenyl]-17-(pentafluoroethyl)estra-4,9-dien-3-one as described below (Compound 2)

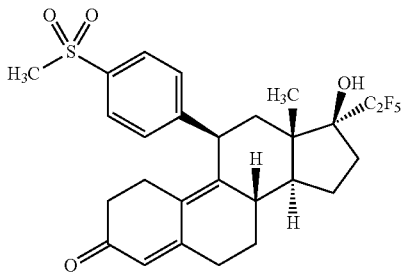

or a pharmaceutically acceptable salt thereof.

The invention prodrugs are as described above.

Preferably, the prodrug is selected from (3α,11β,17β)-11-[4-(methylsulfonyl)phenyl]-17-(pentafluoroethyl)estra-4,9-diene-3,17-diol as described below (Compound 1)

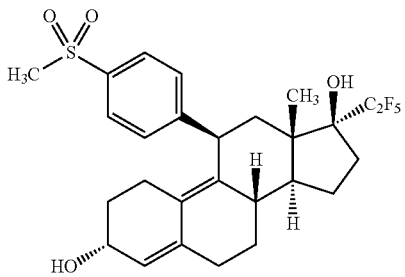

or a pharmaceutically acceptable salt thereof.

In a preferred embodiment, the invention is directed to the use of (3α,11β,17β)-11-[4-(methylsulfonyl)phenyl]-17-(pentafluoroethyl)estra-4,9-diene-3,17-diol (Compound 1) for the manufacture of a therapeutical drug for treating and/or prophylaxis of gynaecological disease or for fertility control and emergency contraception.

Preferably, the gynaecological disease is selected from Uterine Fibroids, Endometriosis and hormone-dependent breast cancers. More preferably, the gynaecological disease is selected from Uterine Fibroids or Endometriosis. Even more preferably, the gynaecological disease is Uterine Fibroids. Even more preferably, the gynaecological disease is Endometriosis.

In other words, the invention is directed to a method for the prophylaxis or treatment of disease(s) comprising the step:

Administering to a mammal an effective amount of (3α,11β,17β)-11-[4-(methylsulfonyl)phenyl]-17-(pentafluoroethyl)estra-4,9-diene-3,17-diol (Compound 1).

Preferably, the prodrug is administered to a patient in need of treatment wherein the administered amount of the prodrug results into the treatment and/or prophylaxis of gynaecological diseases, preferably Uterine Fibroids, Endometriosis or hormone-dependent breast cancers or for fertility control and emergency contraception. Preferably, the gynaecological diseases are selected from Uterine Fibroids or Endometriosis.

In a further embodiment, the invention is directed to the invention prodrug as defined above for use in therapy and/or as prophylaxis.

In a further embodiment, the invention is directed to the invention prodrug as defined above for treating and/or prophylaxis of gynaecological diseases and symptoms thereof or for fertility control and emergency contraception.

Preferably, the gynaecological diseases are selected from Uterine Fibroids and Endometriosis and symptoms thereof.

Most common symptoms related to Uterine Fibroids are pelvic pain, infertility, Heavy Menstrual Bleeding (HMB) and bleeding or spotting between menstruation periods. Preferably, treated symptom is Heavy Menstrual Bleeding (HMB).

Most common symptoms related to Endometriosis are pelvic pain and Dysmenorrhoea (i.e. excessive pain during menstruation), Dyspareunia (i.e. painful sexual intercourse) and infertility. Preferably, treated symptom is Dysmenorrhoea.

The invention prodrug is administered to patient during a period of twelve (12) weeks up to twenty-four (24) weeks followed by a break period wherein administration of Compound 1 is discontinued until one (1) or two (2) menstrual bleeding episodes occur; optionally administration and break periods are repeated at least one (1) time. Treatment is repeated as much as necessary like two (2) to four (4) times. If no menstrual bleeding episode occurs after disruption of treatment then treatment is re-started on demand, due to return of symptoms or disease positively diagnosed, after a break period corresponding to the standard time between two (2) menstrual bleeding episodes (21-45 days).

A menstrual bleeding episode is at least one day of menstrual bleeding.

The invention prodrug is administered daily to patient at the dosage of about 0.5 to 10 mg per unit dosage, preferably 0.5 to 5 mg per unit dosage.

The invention prodrugs are as described above.

In a sixth aspect, the invention is directed to a prodrug activating agent for activating the invention prodrug as defined above where the prodrug activation agent is an isolated Cytochrome P450, preferably the isolated Cytochrome P450 is CYP3A4.

Activating means that the prodrug is converted into an active Selective Progesterone Receptor Modulator (SPRM) useful for treating patient suffering of gynaecological diseases selected from Uterine Fibroids and Endometriosis and symptoms thereof or for enabling fertility control and emergency contraception.

In a further embodiment, the invention is directed to a prodrug activating agent that is combined to the invention prodrug as defined above for use in therapy and/or as prophylaxis as defined above.

In a seventh aspect, the invention is directed to a pharmaceutical composition comprising
  Prodrug activating agent as defined above,
  Prodrug as defined above and
  Optionally admixed with a pharmaceutically acceptable excipient or carrier.

In an eighth aspect, the invention is directed to a method for activating the Prodrug as defined above by contacting the prodrug with the prodrug activating agent. Contacting of the Prodrug with the Prodrug activating agent is occurring in-vivo or in-vitro, preferably in-vitro.

The invention prodrugs are as described above.

Definitions

Prodrugs are chemical entities that undergo enzymatic modifications resulting into a biologically active drug.

Indeed, the chemical entity is metabolized in the body into an active form. Prodrug technology is an important strategy to target drug action to specific cells and tissues and thereby decrease toxicity or side effects on non-target cells. N. Bodor et al., 22 Ann. Rep. Med. Chem. 303-313 (1987); T. Krenitsky et al., 81 P.N.A.S. USA 3209-3213 (1984); J. Hjelle et al., 229 J. Pharmacol. Exp. Ther. 372-380 (1984); S. Magnan et al., 25 J. Med. Chem. 1018-1021 (1982); M. Orlowski et al., 212 J. Pharmacol. Exp. Ther. 167-172 (1980). Prodrugs are inactive or partially active compounds which become therapeutically active by metabolic process(es) in the human or animal body following the intake of the prodrug. Activation of the prodrug can also occur in-vitro.

Prodrugs can be carrier-linked-prodrugs and bioprecursors. The carrier-linked prodrug results from a temporary linkage of the active molecule with a transport moiety. Such prodrugs are less active or inactive compared to the parent active drug. The transport moiety will be chosen for its non-toxicity and its ability to ensure the release of the active principle with efficient kinetics. Whereas the bioprecursors result from a molecular modification of the active principle itself by generation of a new molecule that is capable of being a substrate to the metabolizing enzymes releasing the active principle as a metabolite.

The term reducing agent refers to compound that donates an electron to another species. Common reducing agents include metals potassium, calcium, barium, sodium and magnesium, and also compounds that contain the H ion, those being NaH, LiH, LiAlH4 and CaH2. Sodium borohydride (NaBH4) is a preferred reducing agent.

The term "gynecological diseases" refers to estrogen-dependant conditions selected among the group comprising Uterine Fibroid, Endometriosis, excessive bleeding, abnormal bleeding and dysfunctional bleeding or a combination of one or more of these diseases.

Fibroids are benign non-cancerous tumors that originate from the smooth muscle layer, the myometrium and the accompanying connective tissue of the uterus. Uterine Fibroids are also known as myoma, uterine hypertrophy, uterine leiomyomata, leiomyoma, myoma, fibromyoma, leiofibromyoma, fibroleiomyoma, fibroma, myometrial hypertrophy, fibrosis uteri, and fibrotic metritis. Treatment of Uterine Fibroid(s) shall reduce or shrink the size of fibroid(s) or clear patient from fibroid(s).

Endometriosis is characterized by the presence of endometrium-like tissue outside the uterus cavity, most frequently in the peritoneal cavity. Endometriosis almost exclusively affects pre-menopausal women and is a highly prevalent and highly underdiagnosed condition.

The present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated.

The active ingredient can be dissolved or suspended in a pharmaceutically acceptable liquid carrier such as water, an organic solvent, a mixture of both. The liquid carrier can contain other suitable pharmaceutical additives such as solubilizers, emulsifiers, For oral solid dosage forms (e. g., powders, tablets and capsules), carriers such as starches, sugars, diluents, granulating agents, lubricants, binders can be used as appropriate.

The invention prodrug can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Crennophon®), polyoxethylene fatty acid esters, polyoxyethylene fatty alcohol ethers, glycerol fatty acid esters, poloxamers (such as, for example, Pluronic®), For parenteral administration, the carrier will typically comprise sterile water, although other ingredients that aid in solubility or serve as preservatives may also be prepared, in which case appropriate liquid carriers, suspending agents and the like will be employed. For parenteral administration, the carrier can also be an oily ester such as ethyl oleate.

The term prodrug includes a tautomer, an N-oxide, a hydrate, a solvate, or a pharmaceutically acceptable salt thereof, or a mixture of same.

WO2011/009531A1 is disclosing Selective Progesterone Receptor Modulators (SPRM) of formula I (herein enclosed) and preferred compounds as disclosed below:
(11β,17β)-17-Hydroxy-11-[4-(methylsulphanyl)phenyl]-17-(pentafluoroethyl)estra-4,9-dien-3-one,
(11β,17β)-11-[4-(Ethylsulphanyl)phenyl]-17-hydroxy-17-(pentafluoroethyl)estra-4,9-dien-3-one,
(11β,17β)-17-Hydroxy-11-{4-[(RS)-methylsulphinyl]phenyl}-17-(pentafluoroethyl)estra-4,9-dien-3-one,
(11β,17β)-17-Hydroxy-11-[4-(methylsulphonyl)phenyl]-17-(pentafluoroethyl)estra-4,9-dien-3-one,
(11β,17β)-11-[4-(Ethylsulphonyl)phenyl]-17-hydroxy-17-(pentafluoroethyl)estra-4,9-dien-3-one,
(11β,17β)-11-[4-(Benzylsulphanyl)phenyl]-17-hydroxy-17-(pentafluoroethyl)estra-4,9-dien-3-one,
N-[{4-[(11β,17β))-17-Hydroxy-3-oxo-17-(pentafluoroethyl)estra-4,9-dien-11-yl]phenyl}(RS)(methyl) oxido-λ6-sulphanylidene]-4-methylbenzene sulphonamide,
(11β,17β)-17-Hydroxy-11-[4-(RS-methylsulphonimidoyl) phenyl]-17-(pentafluoroethyl)estra-4,9-dien-3-one,
(11β,17β)-17-Hydroxy-11-[4'-(methylsulphanyl)biphenyl-4-yl]-17-(pentafluoroethyl)estra-4,9-dien-3-one,
(11β,17β)-17-Hydroxy-11-[4'-(methylsulphonyl)biphenyl-4-yl]-17-(pentafluoroethyl)estra-4,9-dien-3-one,
N-[{4'-[(11β,17β)-17-Hydroxy-3-oxo-17-(pentafluoroethyl)estra-4,9-dien-11-yl]biphenyl-4-yl}(RS)(methyl) oxido-λ6-sulphanylidene]-4-methylbenzene sulphonamide, (11β,17β)-17-Hydroxy-11-[4'-(RS-methylsulphonimidoyl)
biphenyl-4-yl]-17-(pentafluoroethyl)estra-4,9-dien-3-
one,
(11β,17β)-17-Hydroxy-17-(pentafluoroethyl)-11-(4'-sul-
phanylbiphenyl-4-yl)estra-4,9-dien-3-one,
4'-[(11β,17β)-17-Hydroxy-3-oxo-17-(pentafluoroethyl)es-
tra-4,9-dien-11-yl]N,N-dimethylbiphenyl-4-sulphona-
mide,
4-[(11β,17β)-17-Hydroxy-3-oxo-17-(pentafluoroethyl)es-
tra-4,9-dien-11-yl]-N,N-dimethylbenzene sulphonamide,
all included herein by reference.

EXPERIMENTAL PART

The following examples are provided to explain the invention without restricting it in anyway.

Example 1: Synthesis of (3α,11β,17β)-11-[4-(methylsulfonyl)phenyl]-17-(pentafluoroethyl)estra-4,9-diene-3,17-diol (Compound 1)

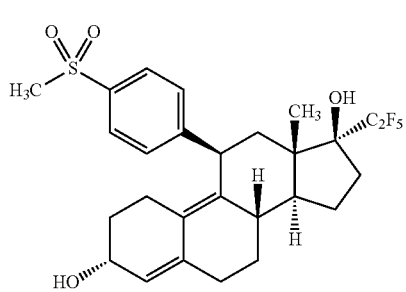

(Compound 1)

MW: 546.60 g/mol; MF: $C_{27}H_{31}F_5O_4S$ a) Production of the Starting Material The production of (11β,17β)-17-hydroxy-11-[4-(methylsulfonyl)phenyl]-17-(pentafluoroethyl)estra-4,9-dien-3-one (CAS-No. 1262108-14-4; Compound 2) is described in WO2011/009531 and DE 102009034362 and can be carried out by analogy with the instructions contained therein.

b) Production of (3α,11β,17β)-11-[4-(methylsulfonyl)phenyl]-17-(pentafluoroethyl)estra-4,9-diene-3,17-diol (Compound 1)

50 g (11β,17β)-17-hydroxy-11-[4-(methylsulfonyl)phenyl]-17-(pentafluoroethyl) estra-4,9-dien-3-one (Compound 2) are dissolved in 500 ml methanol. 3.5 g (1 equiv.) sodium borohydride are added in portions at 0-5° C. whilst stirring. After a reaction time of about 6 hours at 5° C., 170 ml water are slowly added, the resulting mixture is stirred for 1 hour and filtered. The filter cake is dried for 16 hours at 45° C. in a vacuum. Interim yield: 46.9 g (mixture of Compound 1 and the 3-beta isomer in a ratio of ~2:1).

45.9 g of the above diastereoisomer mixture dissolved in 462 ml dichloromethane and 76 ml methanol were chromatographed in 78 injections on 500 g Kromasil Diol 10MYM/60A with n-hexane/ethyl acetate (55:45 v/v) (column diameter 80 mm, flow rate 160 ml/min, 22° C.+/−3° C.). The desired fractions were each collected, cleaned and concentrated to dryness in a vacuum. The residue was dried in a high vacuum. Yield: 25.9 g (3α,11β,17β)-11-[4-(methylsulfonyl)phenyl]-17-(pentafluoro-ethyl)estra-4,9-diene-3,17-diol (Compound 1).

MS (ESI, neg. mode): 591 m/z (M-H$^+$+HCOOH)

$^1$H-NMR (D6-DMSO; 500.13 MHz): 7.82 ppm (d, 2H, aromat.), 7.46 ppm (d, 2H, aromat.), 5.76 ppm (s, 1H, OH), 5.42 ppm (bs, 1H, olefin. 4-H), 4.62 ppm (d, 1H, OH), 4.48 ppm (m, 1H, benzyl. H-11), 4.08 ppm (m, 1H, H-3), 3.18 ppm (s, 3H, CH3-SO2-), 2.58 bis 1.15 ppm (several m, 16H), 0.44 ppm (s, 3H, CH3)

$^{13}$C-NMR (D6-DMSO; 125.8 MHz): 152.28 ppm (s, quart.), 137.73 ppm (s, quart.), 134.05 ppm (s, quart.), 133.13 ppm (s, quart.), 130.87 ppm (s, quart.), 128.03 ppm (s, CH), 127.86 ppm (s, CH), 126.78 ppm (s, CH), 122-114 ppm (complex m, CF3-CF2-), 83.21 (t, quart., C-17), 65.20 ppm (s, CH, C-3), 51.46 ppm (d, CH), 50.09 ppm (s, quart., C-13), 43.51 ppm (s, CH3-SO2-), 39.48 ppm (s, CH, C-11), 38.63 ppm (d, CH2), 38.22 ppm (s, CH), 32.48 ppm (s, CH2), 32.28 ppm (s, CH2), 29.90 ppm (s, CH2), 28.35 ppm (s, CH2), 24.60 ppm (s, CH2), 23.74 ppm (s, CH2), 16.29 ppm (s, CH3).

Example 2: Abortion Test in Female Rats

The abortive test (=abortifacient activity in the early pregnancy of the rat) reported here is the premise that progesterone is essential for an undisturbed pregnancy in all phases of an intra-uterine pregnancy of mammals. For that reason compounds with progesterone antagonistic activity are effective through blockade of the progesterone receptors in the endometrium. This leads to termination of pregnancy.
Study Design and Method
Species and strain: Wistar Han rat
Sex and age: female, 9-14 weeks old
Body weight: 180-200 g
Breeder: Charles River, 97633 Sulzfeld, Germany
Supplier: Charles River, 97633 Sulzfeld, Germany
Room temperature: 20-22° C.
Relative humidity: 50-70%
Light period: artificial light; 12-hour day (from 06.00 a.m. to 06.00 p.m.), 12-hour night cycle.
Maintenance conditions: conventionally housed in air-conditioned animal rooms
Caging: animals were kept in Makrolon® cages type IV
Feed type: Ssniff®, pelleted
Feeding time: ad libitum
Water type: tab water via water bottles
Watering time: ad libitum Rats were delivered after mating at d2 (=day 2 of pregnancy, =d2 p.c.) directly from the animal supplier. Afterwards the animals were randomized to treatment or control groups. The animals received the test compound or vehicle orally once daily from day 5-7 of pregnancy. On the day of autopsy (d9) the animals were sacrificed with $CO^2$. Study was performed with different dosages of test compound that was Compound 1.

From day 5-7 of pregnancy 6 animals in a group received the same dose of Compound 1 orally once daily in the morning. There were 4 treatment groups, with dosages of 0.05, 0.2, 0.5, 2.0, 5.0 and 10.0 mg/kg day of Compound 1 and a vehicle only group.

The progesterone-antagonistic activity was analyzed as follows: The absence of implantation sites was assessed as complete abortion, the presence of regressed and/or hemorrhagic implantation sites (so defined as pathological nidation sites) as incomplete abortion. The total rate of abortion indicates the percentage of animals per group affected by an abortive event (either by pathological implantation sites or by complete abortions).

Results:

After oral administration of Compound 1 at doses of 0.5 mg/kg/day, 1 mg/kg/day, 2 mg/kg/day, 5 mg/kg/day and 10 mg/kg/day, in all animals abortive events have been proven (=total rate of abortion: 100%). At 0.2 mg/kg/d only one animal out of six showed pathological implantation sites and 5 animals were unaffected. See Table 1.

TABLE 1

PR antagonistic activity of Compound 1 in termination of early pregnancy in rats after oral (N = 6 animals/group) administration.

| Compound | Route of application | Dose [mg/kg * day] | Total rate of abortion [%] | Complete abortion [%] | Pathological nidation sites [%] |
|---|---|---|---|---|---|
| Compound 1 | p.o. | 0.05 | 0 | 0 | 0 |
| Compound 1 | p.o. | 0.2 | 17 | 0 | 17 |
| Compound 1 | p.o. | 0.5 | 100 | 50 | 50 |
| Compound 1 | p.o. | 1.0 | 100 | 83 | 17 |
| Compound 1 | p.o. | 2.0 | 100 | 100 | 0 |
| Compound 1 | p.o. | 5.0 | 100 | 100 | 0 |
| Compound 1 | p.o. | 10.0 | 100 | 100 | 0 |
| vehicle | p.o. | — | 0 | 0 | 0 |

WO2011/009531 reported for Compound 2 similar abortion events.

Example 3: Plasma Concentrations and Pharmacokinetic Parameters of Compounds 1 and 2

Study Design and Method

Under the same conditions as described in Example 2 three single dosages of Compound 1 (0.2, 1.0 and 5 mg/kg/day) were administered to rats. Blood samples were taken from the rats at several time-points (1, 2, 4, 7 and 24 h, N=3 animals at each time-point), to allow for calculation of AUC (0-24) and $C_{max}$ of compound 1 and compound 2 in rat plasma. The plasma samples were stored at −15° C. until analysis. Compound 1 and 2 were determined in plasma after protein precipitation with acetonitrile containing the internal standards for compound 1 and compound 2. The supernatant was analyzed by separation employing high-pressure liquid chromatography and tandem mass spectrometric detection. The lower limit of quantitation (LLOQ) for Compound 1 was 1.00 μg/L, the linear range between 1.00 and 200 μg/L. The lower limit of quantitation (LLOQ) for Compound 2 was 0.200 μg/L, the linear range between 0.200 and 200 μg/L. A sample volume of 0.1 mL plasma was used.

The precision for Compound 1 ranged between 0.97 and 3.73%, accuracy between 99.8 and 101.3%, for Compound 2 precision ranged between 2.01 and 6.19%, accuracy between 92.3 and 96.6% calculated from the study quality control samples.

Results

The maximum concentration of Compound 2 in rat plasma after single oral administration of Compound 1 to female rats was found to be 10.5 μg/L (0.2 mg/kg), 66 μg/L (1.0 mg/kg) and 235 μg/L (5.0 mg/kg), respectively. The AUC (0-24 h) was 90.6 μg*h/L (0.2 mg/kg), 435 μg*h/L (1.0 mg/kg) and 2060 μg*h/L (5.0 mg/kg). Only very low amount of remaining compound 1 was detected in rat plasma with maximum concentration of <1.00 μg/L (0.2 mg/kg), 3.36 μg/L (1.0 mg/kg) and 12.9 μg/kg (5.0 mg/kg), respectively. No AUC of compound 1 could be calculated (see Table 2).

These results indicate an intensive metabolic conversion of Compound 1 to Compound 2 in rats.

Hence, the efficacy of Compound 1 observed in the current test model is due to Progesterone Receptor Antagonistic activity of Compound 2 which was formed metabolically in rats. The marginal exposure of Compound 1 observed after its administration to rats indicated, that Compound 1 has a negligible contribution to the efficacy measured in the abortion test in rat.

TABLE 2

| Test Compound | Route of application | Dose [mg/kg * day] | Compound 1 Cmax [μg/L]] | Compound 1 AUC (0-24 h) [μg * h/L] | Compound 2 Cmax [μg/L]] | Compound 2 AUC (0-24 h) [μg * h/L] |
|---|---|---|---|---|---|---|
| Compound 1 | p.o. | 0.2 | <1.00 | n.c. | 10.5 | 90.6 |
| Compound 1 | p.o. | 1.0 | 3.36 | n.c. | 66 | 435 |
| Compound 1 | p.o. | 5.0 | 12.9 | n.c. | 235 | 2060 |

Compound 1 is almost completely converted into Compound 2 in rat.

Example 4: Progesterone Receptor (PR) Transactivation Assay of Compounds 1 and 2

Compound 1: Method

A transactivation assay was carried out in SK-N-MC cells (human neuroblastoma cells) stably transfected with a plasmid expressing the human PR-A (pRChPR-A-neo) and a reporter gene (LUC) linked to a hormonally responsive promoter (MMTV). Pre serum-starved cells were grown for 16 hrs. either in the absence (negative control) or presence of increasing concentrations of Compound 1 (5.1 pmol/L, 26 pmol/L, 0.13 nmol/L; 0.64 nmol/L, 3.2 nmol/L, 16 nmol/L, 80 nmol/L, 400 nmol/L, 2 umol/L and 10 pmol/L), to determine agonistic activity. As a positive control for reporter gene induction, cells were treated with the synthetic progestin promegestone (10 pmol/L, 30 pmol/L, 91 pmol/L, 0.27 nmol/L, 0.82 nmol/L, 2.5 nmol/L, 7.4 nmol/L, 22 nmol/L, 67 nmol/L, 200 nmol/L). For the determination of antagonistic activity, cells were treated with 0.1 nmol/L promegestone and in addition, with increasing concentrations of Compound 1 (5.1 pmol/L, 26 pmol/L, 0.13 nmol/L; 0.64 nmol/L, 3.2 nmol/L, 16 nmol/L, 80 nmol/L, 400 nmol/L, 2 umol/L and 10 pmol/L). As a positive control for inhibition of reporter gene transcription, cells were cultured with increasing concentrations of the antiprogestin mifepristone (10 pmol/L, 30 pmol/L, 91 pmol/L, 0.27 nmol/L, 0.82 nmol/L, 2.5 nmol/L, 7.4 nmol/L, 22 nmol/L, 67 nmol/L, 200 nmol/L). LUC activity (LUC=luciferase) was determined in cell lysates and is measured as RLU (relative light units).

TABLE 3

| Progesterone receptor A (PR-A) | Potency IC$_{50}$ [nmol/l] |
|---|---|
| Compound 1 | 5.3 |

Compound 2: Method as described in WO2011/009531

SK-N-MC cells (human neuroblastoma cells), which have been stably transfected with plasmids, which express the human progesterone receptor B (pRChPR-α-neo) or the human progesterone receptor A (pRChPR-A-neo) and a reporter construct (pMMTV-LUC), were incubated for 24 hours either in the absence (negative control) or in the presence of increasing amounts of the respective Compound 2 (0.01 nmol/l, 0.1 nmol/l, 1 nmol/l, 10 nmol/l, 100 nmol/l and 1 pmol/l), in order to determine the agonistic efficacy. As positive control of reporter gene induction, the cells were treated with the synthetic gestagen promegestone (0.01 nmol/l, 0.1 nmol/l, 1 nmol/l, 10 nmol/l, 100 nmol/l and 1 pmol/l). For determination of the antagonistic activity, the cells were treated with 0.1 nmol/l promegestone and additionally with increasing amounts of the respective test compound (0.01 nmol/l, 0.1 nmol/l, 1 nmol/l, 10 nmol/l, 100 nmol/l and 1 pmol/l). The activity of the LUC reporter gene (LUC=luciferase) was determined in the cell lysates and was measured as RLU (relative light units).

TABLE 4

| Progesterone receptor A (PR-A) | Potency IC$_{50}$ [nmol/l] |
|---|---|
| Compound 2 | 0.096 |

Results:

Compound 2 is a very strong antagonist on both PR isoforms, PR-A and PR-B, with no agonistic activity with an IC$_{50}$ of 0.096 nM for PR-A.

Compound 1 exhibits a significantly lower antagonistic activity than Compound 2. The IC$_{50}$ is 5.3±1.43 nM for PR-A.

Example 5: In Vitro Metabolism of 14C-Labeled (3α,11β,17β-11-[4-(methylsulfonyl)phenyl]-17-(pentafluoroethyl)estra-4,9-diene-3,17-diol (Compound 1) in Human Liver Microsomes Human liver microsomes were incubated with (3α,11β,17β)-11-[4-($^{14}$C-methylsulfonyl)phenyl]-17-(pentafluoroethyl)estra-4,9-diene-3,17-diol (Compound 1).

| Incubation buffer | 50 mM potassium diphosphate (pH 7.4) |
|---|---|
| NADPH generating system | 1.2 mM NADPH |
| | 8 mM glucose-6-phosphate |
| | 38 mM KCl |
| | 5 mM MgCl solution |
| | 100 U/mL glucose-6-phosphate dehydrogenase |
| Temperature | 37° C. shaking water bath, 90 rpm |
| Substrate | 1 μM (3α,11β,17β)-11-[4-(methylsulfonyl)phenyl]-17-(pentafluoroethyl)estra-4,9-diene-3,17-diol from a stock solution with 0.1 mM in acetonitrile |
| Protein concentration | 0.5 mg/mL |
| Measurement times | 0, 0.25, 0.5, 0.75 h |
| Incubation volume | 250 μL |

The incubation mixture containing buffer, reconstituting system and microsomal protein was preincubated at 37° C. for 3 min. Incubation was started by the addition of the solution containing (3α,11β,17β)-11-[4-(methylsulfonyl)phenyl]-17-(pentafluoroethyl)estra-4,9-diene-3,17-diol (Compound 1). The samples were incubated at 37° C. in a continuously operating shaking water bath. The incubation reaction was stopped by the addition of 160 μL acetonitrile. The stopped incubations were centrifuged for 10 minutes at 13000 rpm (4° C.) and stored at −18° C. until they were subsequently analysed. 50 μL of the supernatant was examined by chromatography and detected by radiometry and mass spectrometry.

As a result of this examination a marked decrease was observed in the proportion of (3α,11β,17β)-11-[4-(methylsulfonyl)phenyl]-17-(pentafluoroethyl)estra-4,9-diene-,17-diol (Compound 1) after 1 hours incubation compared to the sample before the start of incubation (0 hr). A large quantity of (11β,17β)-17-hydroxy-11-[4-(methylsulfonyl)phenyl]-17-penta-fluoroethyl)estra-4,9-dien-3-one (Compound 2) had formed in the incubation sample after 1 hour. This was identified in the samples by mass spectrometric parameters (precise molecular mass [M-H]=543.162847, MS/MS fragments of m/z 543: 527, 487, 466, 448, 376, 349, 315, 236, 163) and the retention time in the radio chromatogram as well as in the mass chromatogram. These parameters correspond to those of the synthetically produced (11β,17β)-17-hydroxy-11-[4-(methylsulfonyl)phenyl]-17-(pentafluoroethyl)estra-4,9-dien-3-on (Compound 2). See FIG. 1.

FIG. 1: Concentration-time course of Compound 2 and Compound 1 after incubation of Compound 1 in human liver microsomes Example 6: Plasma Concentrations of Compound 3 (WO2011/009531A2 Example 8 Sulfoximine) and its Proposed Metabolite Compound 2, Study Design and Method Under the same conditions as described in Example 3, Compound 3 (5 mg/kg/day) was administered to female rats at a dose of 5 mg/kg. Blood samples were taken from the rats at several time-points (0.5, 1, 3, 6 h, N=3 animals at each time-point), to allow for calculation of AUC (0-inf) of compound 3 and compound 2 in rat plasma.

The plasma samples were stored at −15° C. until analysis. Compound 3 and compound 2 were determined in plasma after protein precipitation with acetonitrile containing the internal standards for compound 3 and compound 2. The supernatant was analyzed by separation employing high-pressure liquid chromatography and tandem mass spectrometric detection. AUC (0-inf) means Area Under the plasma Concentration vs. time curve (0-inf) from zero to infinity.

Results

The exposure in terms of AUC (0-inf) of Compound 3 in rat plasma after single oral administration of 5 mg/kg of compound 3 to female rats was found to be 1235 μg*h/L. The exposure in terms of AUC (0-inf) of Compound 2 in rat plasma after single oral administration of 5 mg/kg of compound 3 to female rats was found to be 586 μg*h/L (see Table 5). These results indicate a metabolic conversion of Compound 3 into Compound 2 in rats. Hence, efficacy of Compound 3 could partly due to Progesterone Receptor Antagonistic activity of Compound 2 which was formed metabolically in rats.

TABLE 5

| Test Compound Administered | Route of application | Dose [mg/kg * day] | Compound 3 AUC (0-inf) [μg * h/L] | Compound 2 AUC (0-inf) [μg * h/L] |
| --- | --- | --- | --- | --- |
| Compound 3 | p.o. | 5 mg/kg | 1235 | 586 |

Table 5 shows that Compound 3 is partially converted into Compound 2 in rat.

Example 7: In Vitro Metabolism of 14C-Labeled (3α,11β,17β)-11-[4-(methylsulfonyl)phenyl]-17-(pentafluoroethyl)estra-4,9-diene-3,17-diol (Compound 1) in Recombinant Human CYP3A4 Enzyme Recombinant human CYP3A4 was incubated with (3α,11β,17β)-11-[4-($^{14}$C-methylsulfonyl)phenyl]-17-(pentafluoroethyl)estra-4,9-diene-3,17-diol (Compound 1).

| | |
| --- | --- |
| Incubation buffer | 50 mM potassium diphosphate (pH 7.4) |
| NADPH generating system | 1.2 mM NADPH<br>8 mM glucose-6-phosphate<br>38 mM KCl<br>5 mM MgCl solution<br>100 U/mL glucose-6-phosphate dehydrogenase |
| Temperature | 37° C. shaking water bath |
| Substrate | 1 μM (3α,11β,17β)-11-[4-(methylsulfonyl)phenyl]-17-(pentafluoroethyl)estra-4,9-diene-3,17-diol from a stock solution with 0.1 mM in acetonitrile |
| Protein concentration | 100 pmol/mL |
| Measurement times | 0, 0.5, 2 h |
| Incubation volume | 400 μL |

The incubation mixture containing buffer, reconstituting system and CYP3A4 protein was prepared and given into a 37° C. shaking water bath. Incubation was started by the addition of the solution containing (3α,11β,17β)-11-[4-(methylsulfonyl)phenyl]-17-(pentafluoroethyl)estra-4,9-diene-3,17-diol (Compound 1). The samples were incubated at 37° C. in a continuously operating shaking water bath. 200 μL of the incubation mixture were removed after incubation time and the reaction was stopped by the addition of 120 μL acetonitrile on an ice bath. The stopped incubations were centrifuged for 10 minutes at 12000 rpm (7° C.). After removing of the supernatant from the protein pellet the supernatant was stored at −20° C. until they were subsequently analysed. 50 μL of the supernatants was examined by chromatography and detected by radiometry and mass spectrometry.

As a result of this examination a marked decrease was observed in the proportion of (3α,11β,17β)-11-[4-(methylsulfonyl)phenyl]-17-(pentafluoroethyl)estra-4,9-diene-,17-diol (Compound 1) after 0.5 and 2 hours incubation compared to the sample before the start of incubation (0 hr). A large quantity of (11β,17β)-17-hydroxy-11-[4-(methylsulfonyl)phenyl]-17-penta-fluoroethyl)estra-4,9-dien-3-one (Compound 2) had formed in the incubation sample after 30 hour. This was identified in the samples by mass spectrometric parameters (precise molecular mass [M-H] =543.162847, MS/MS fragments of m/z 543: 527, 487, 466, 448, 376, 349, 315, 236, 163) and the retention time in the radiochromatogram as well as in the mass chromatogram. These parameters correspond to those of the synthetically produced (11β,17β)-17-hydroxy-11-[4-(methylsulfonyl)phenyl]-17-(pentafluoroethyl)estra-4,9-dien-3-on (Compound 2). Furthermore, after 120 min of incubation the amount of compound 2 decreased remarkably with formation of a complex pattern of its oxidation and reduction products.

The results indicate that the formation of compound 2 from compound 1 is mainly catalyzed by the CYP3A4 enzyme.

TABLE 6

In vitro metabolism of Compound 1 with rhCYP3A4 enzyme (% of 14C-radioactivity of compound 1 and compound 2 in incubation samples)

| Incubation time with rhCYP3A4 [h] | Compound 1 (%) | Compound 2 (%) | Other metabolites of Compound 1 identified (%) |
| --- | --- | --- | --- |
| 0 | 82 | 9.1 | 5.5 |
| 0.5 | 52 | 36 | 13 |
| 2 | 2.7 | 16 | 81 |

Example 8: Plasma Concentrations of Compound 1 in Human with and without Co-Administration of Itraconazole, Study Design and Method Compound 2 was administered to 14 healthy postmenopausal women as a single oral dose of 4 mg. Thereafter, 200 mg daily oral dose of Itraconazole (strong inhibitor of CYP3A4) was administered to the same 14 subjects over 14 days. Compound 2 was administered again as a single oral dose of 4 mg to the same 14 subjects together with the 4$^{th}$ dose of Itraconazole. The pharmacokinetic profiles of compound 2 as well as of compound 1 were determined in human plasma with and without co-medication with Itraconazole.

The plasma samples were stored at −80° C. until analysis. Compound 1 and compound 2 were determined in human plasma after protein precipitation with acetonitrile containing the internal standards for compound 1 and compound 2. The supernatant was analyzed by separation employing high-pressure liquid chromatography and tandem mass spectrometric detection.

Results

The exposure in terms of AUC (0-inf) of compound 1 in human plasma after single oral administration of 4 mg of compound 2 to women was found to be 18.7 μg*h/L without co-medication and 409 μg*h/L after co-medication with Itraconazole.

The data indicate a strong increase of exposure of compound 1 in humans in the presence of Itraconazole known to be a strong inhibitor of the activity of CYP3A4.

The results indicate that the formation of compound 2 starting from compound 1 is mainly catalyzed by the CYP3A4 enzyme.

TABLE 7

| Test Compound | Route of application | Dose [mg] | Compound 1 AUC (0-inf) [μg * h/L] | Compound 1 with Itraconazole AUC (0-inf) [μg * h/L] |
| --- | --- | --- | --- | --- |
| Compound 2 | p.o. | 4 | 18.7 | 409 |

Example 9: In vitro Metabolism of 14C-labeled (11β,17β)-17-Hydroxy-11-[4-(methylsulphonyl) phenyl]-17-(pentafluoroethyl)estra-4,9-dien-3-one (Compound 2) in Human Liver Cytosol Human liver cytosol was incubated with (11β,17β)-17-Hydroxy-11-[4-(methylsulphonyl)phenyl]-17-(pentafluoroethyl)estra-4,9-dien-3-one (Compound 2).

| | |
|---|---|
| Incubation buffer | 50 mM potassium diphosphate (pH 7.4) |
| NADPH generating system | 1.2 mM NADPH |
| | 8 mM glucose-6-phosphate |
| | 38 mM KCl |
| | 5 mM MgCl solution |
| | 100 U/mL glucose-6-phosphate dehydrogenase |
| Temperature | 37° C. shaking water bath, 90 rpm |
| Substrate | 10 μM (11β,17β)-17-Hydroxy-11-[4-(methylsulphonyl)phenyl]-17-(pentafluoroethyl)estra-4,9-dien-3-one from a stock solution with 0.1 mM in acetonitrile |
| Protein concentration | 1.0 mg/mL |
| Measurement times | 0, 1, and 4 h |
| Incubation volume | 1000 μL |

The incubation mixture containing buffer, reconstituting system and cytosolic protein was preincubated at 37° C. for 3 min. Incubation was started by the addition of the solution containing (11β,17β)-17-Hydroxy-11-[4-(methylsulphonyl)phenyl]-17-(pentafluoroethyl)estra-4,9-dien-3-one (Compound 2). The samples were incubated at 37° C. in a continuously operating shaking water bath. 250 μL of the incubation mixture was stopped by the addition of 100 μL acetonitrile. The stopped incubations were centrifuged for 10 minutes at 13000 rpm (4° C.) and stored at −18° C. until they were subsequently analysed. 50 μL of the supernatant was examined by chromatography and detected by radiometry and mass spectrometry. As a result of this examination a marked decrease was observed in the proportion of (11β,17β)-17-Hydroxy-11-[4-(methylsulphonyl)phenyl]-17-(pentafluoroethyl)estra-4,9-dien-3-one (Compound 2) after 1 and 4 hours incubation time compared to the sample before the start of incubation (0 hr).

A significant quantity of (3α,11β,17β)-11-[4-(methylsulfonyl)phenyl]-17-(pentafluoroethyl)-estra-4,9-diene-,17-diol (Compound 1) had formed in the incubation sample after 1 and 4 hours. This was identified in the samples by mass spectrometric parameters (precise molecular mass [M-H]=545.1801, MS/MS fragments of m/z 545: 527, 463, 407) and the retention time in the radio chromatogram as well as in the mass chromatogram. These parameters correspond to those of the synthetically produced (3α,11β, 17β)-11-[4-(methylsulfonyl)phenyl]-17-(pentafluoroethyl)-estra-4,9-diene-,17-diol (Compound 1). See FIG. 2. No turnover of Compound 2 to Compound 1 in liver cytosol was detected in the absence of NADPH generating system as well as in the presence of the NAD co-factor.

Figure 2:
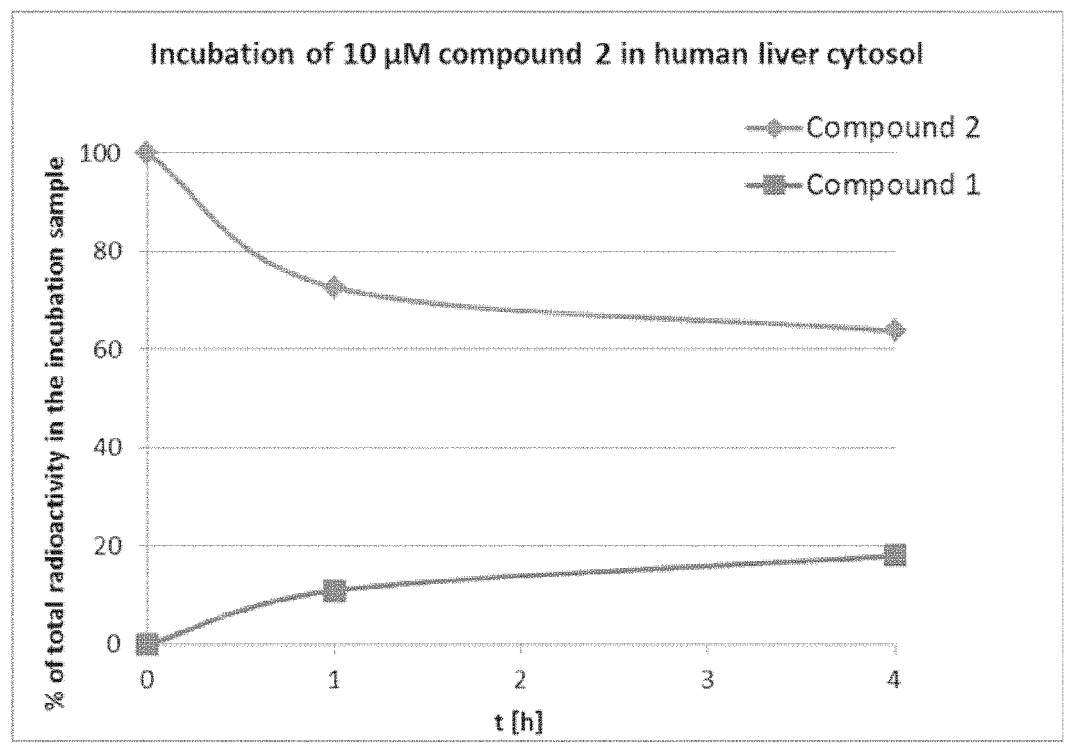
FIG. 2 depicts concentration-time course of Compound 1 and Compound 2 after incubation of Compound 2 in human liver cytosolic fraction.

FIG. 2: Concentration-time course of Compound 1 and Compound 2 after incubation of Compound 2 in human liver cytosolic fraction.

In human liver cytosolic fraction with NADPH the major metabolic pathway of Compound 2 was the formation of the primary reduction product Compound 1 (3-α-hydroxy derivative). These data indicate, that the formation of Compound 1 is catalyzed by cytosolic Aldo-Keto Reductase (AKR) as these AKRs are situated in the cytosolic fraction of human liver cells and act in a NADPH-dependent manner.

Example 10: Synthesis of (11β,17β)-17-hydroxy-11-[4-(RS-methylsulphonimidoyl)phenyl]-17-(pentafluoroethyl)estra-4,9-dien-3-one (Compound 3)

Compound 3 synthesis is described in WO2011/009531.

The invention claimed is:
1. A prodrug of a Selective Progesterone Receptor Modulator (SPRM), wherein the SPRM is (11β,17β)-17-Hydroxy-11-[4-(methylsulphonyl)phenyl]-17-(pentafluoroethyl)estra-4,9-dien-3-one

(Compound 2)

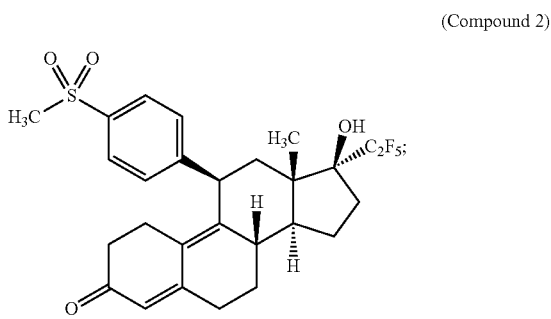

and
wherein the prodrug is (3α,11β, 17β)-11-[4-(methylsulfonyl)phenyl]-17-(pentafluoroethyl)estra-4,9-diene-3,17-diol (Compound 1)

(Compound 1)

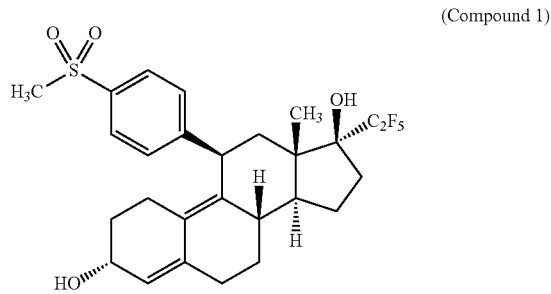

or a pharmaceutically acceptable salt thereof.
2. A pharmaceutical composition comprising the prodrug according to claim 1, optionally admixed with a pharmaceutically acceptable excipient or carrier.
3. A method for fertility control and emergency contraception comprising administering to a patient an effective amount of a prodrug according to claim 1.
4. A method for the treatment of a gynaecological disease, or a symptom thereof, comprising administering to a patient an effective amount of a prodrug according to claim 1.
5. The method according to claim 4 wherein the gynaecological disease is selected from the group consisting of Uterine Fibroids, Endometriosis, and symptoms thereof.
6. A method for producing the prodrug according to claim 1, which method comprises reacting (11β,17β)-17-hydroxy-11-[4-(methylsulfonyl)phenyl]-17-(pentafluoroethyl)estra-4,9-dien-3-one (Compound 2) in the presence of a reducing agent.
7. The method according to claim 6 wherein the prodrug is produced by a reaction that is catalyzed by an isolated Aldo-Keto Reductase (AKR) enzyme.

8. A pharmaceutical composition comprising
an isolated Cytochrome P450,
a prodrug according to claim 1, and
a pharmaceutically acceptable excipient or carrier.

9. An ex vivo method for activating the prodrug according to claim 1, which method comprises contacting the prodrug with an activating agent, wherein the activating agent is an isolated Cytochrome P450.

10. The method according to claim 6 wherein the reducing agent is sodium borohydride.

11. The pharmaceutical composition according to claim 8, wherein the isolated Cytochrome P450 is CYP3A4.

12. The method of claim 9, wherein the isolated cytochrome P450 is CYP3A4.

* * * * *